US011650611B2

United States Patent
Janich et al.

(10) Patent No.: US 11,650,611 B2
(45) Date of Patent: May 16, 2023

(54) ELECTROSURGICAL GENERATOR

(71) Applicant: OLYMPUS WINTER & IBE GMBH, Hamburg (DE)

(72) Inventors: Fabian Janich, Potsdam (DE); Jelle Dijkstra, Berlin (DE); Frank Breitsprecher, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 96 days.

(21) Appl. No.: 17/215,200

(22) Filed: Mar. 29, 2021

(65) Prior Publication Data

US 2021/0303015 A1    Sep. 30, 2021

(30) Foreign Application Priority Data

Mar. 27, 2020   (DE) .......................... 102020108601.6

(51) Int. Cl.
*G05F 1/625* (2006.01)
*H02J 4/00* (2006.01)
(Continued)

(52) U.S. Cl.
CPC .......... *G05F 1/625* (2013.01); *A61B 18/1206* (2013.01); *H02J 4/00* (2013.01);
(Continued)

(58) Field of Classification Search
CPC ................ G05F 1/625; A61B 18/1206; A61B 2018/0072; A61B 2018/00767;
(Continued)

(56) References Cited

U.S. PATENT DOCUMENTS 5,836,943 A * 11/1998 Miller, III .......... A61B 18/1206
606/34
2004/0095100 A1 * 5/2004 Thompson ......... A61B 18/1206
322/32
(Continued)

FOREIGN PATENT DOCUMENTS

DE      696 36 102 T2    12/2006
EP       1 082 944 B1     5/2006

OTHER PUBLICATIONS

Feb. 12, 2021 Office Action issued in German Patent Application No. 102020108601.6.

*Primary Examiner* — John W Poos
*Assistant Examiner* — Tyler J Pereny
(74) *Attorney, Agent, or Firm* — Oliff PLC

(57) ABSTRACT

An electrosurgical generator with a high-voltage power supply that supplies a DC output voltage receives the DC output voltage of the high-voltage power supply and generates a high-frequency AC output voltage. When generator is operating, a control unit receives signals from an AC output voltage measuring unit and current measuring unit. The control unit limits an increase of DC output voltage of the high-voltage power supply as soon one predefined maximum value is reached or exceeded. When the generator is operating, the control unit configured to receive signals from a DC output voltage measuring unit that represent a respective current value of the DC output voltage, and to compare a respective current value of DC output voltage with a predefined minimum value for DC output voltage, and to cause the DC output voltage of the high-voltage power supply to increase as soon as it falls below the predefined minimum value.

13 Claims, 4 Drawing Sheets

Figure 1:
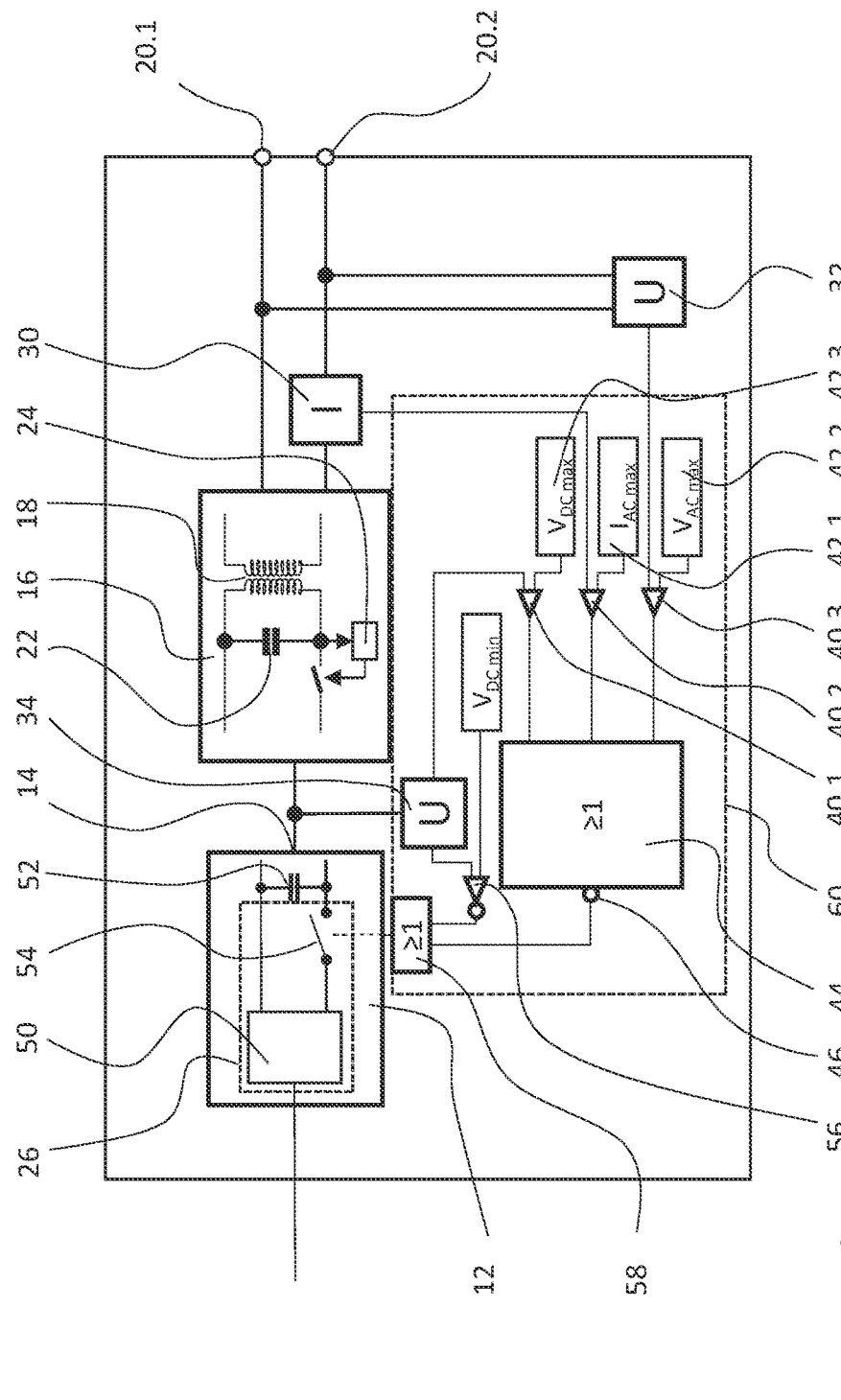

(51) Int. Cl.
*H03K 5/24* (2006.01)
*A61B 18/12* (2006.01)
*A61B 18/00* (2006.01)

(52) U.S. Cl.
CPC ........ *H03K 5/24* (2013.01); *A61B 2018/0072* (2013.01); *A61B 2018/00767* (2013.01); *A61B 2018/1266* (2013.01)

(58) Field of Classification Search
CPC .. A61B 2018/1266; A61B 2018/00648; A61B 2018/00708; A61B 2018/00827; A61B 18/1233; A61B 2018/00601; A61B 2018/00607; A61B 2018/00625; A61B 2018/00892; H02J 4/00; H03K 5/24
See application file for complete search history.

(56) References Cited

U.S. PATENT DOCUMENTS

2011/0163711 A1* 7/2011 Kiss ................ H01M 10/46
320/101
2013/0066311 A1 3/2013 Smith et al.

* cited by examiner

ELECTROSURGICAL GENERATOR

The invention relates to an electrosurgical generator with a high-voltage power supply that supplies a DC output voltage during operation, and with a high-frequency part that receives the DC output voltage from the high-voltage power supply during operation, generates a high-frequency AC output voltage and supplies it to the outputs of the electrosurgical generator.

Electrosurgery can be used for cutting, coagulating (obliterating) and/or vaporizing biological tissue, i. e. body tissue. High-frequency alternating currents with a frequency between 0.2 MHz and 3 MHz are typically used in electrosurgery.

An electrosurgical system generally comprises an electrosurgical generator for generating the high-frequency alternating current. As a general rule, the electrosurgical generator has two outputs where an electrosurgical instrument can be connected, and a high-frequency AC voltage is provided between these outputs during operation. In addition, an electrosurgical generator usually comprises a high-voltage power supply that generates a direct voltage during operation, and a high-frequency part that is connected to the high-voltage power supply and generates a high-frequency alternating current from the direct voltage during operation.

The task upon which the invention is based is to expand the range of applications of an electrosurgical generator.

For this purpose, the invention proposes an electrosurgical generator with a high-voltage power supply that supplies a DC output voltage during operation, and with a high-frequency part that receives the DC output voltage from the high-voltage power supply during operation, generates a high-frequency AC output voltage and supplies it to the outputs of the electrosurgical generator; this electrosurgical generator comprises a control unit for controlling the high-voltage power supply, as well as at least one AC output voltage measuring unit and one AC output current measuring unit. The control unit, the AC output voltage measuring unit and the AC output current measuring unit are configured and connected in such a way that, when the electrosurgical generator is in operation, the control unit receives signals respectively from the AC output voltage measuring unit and the AC output current measuring unit that represent a respective current value of the AC output voltage and the AC output current. The control unit is configured to compare the respective current values of the AC output voltage and the AC output current with predefined maximum values for the AC output voltage and the AC output current, and to limit an increase of the DC output voltage of the high-voltage power supply as soon as at least one predefined maximum value for the AC output voltage or the AC output current, or a value derived from these values, is reached or exceeded. The electrosurgical generator further comprises a DC output voltage measuring unit for measuring the DC output voltage of the high-voltage power supply. The DC output voltage measuring unit is connected to the control unit, and the control unit is configured to receive, when the electrosurgical generator is in operation, signals from the DC output voltage measuring unit that represent a respective current value of the DC output voltage. Furthermore, the control unit is configured to compare a respective current value of the DC output voltage with a predefined minimum value for the DC output voltage, and to cause the DC output voltage of the high-voltage power supply to increase as soon as it falls below the predefined minimum value for the DC output voltage.

In order to cause the DC output voltage of the high-voltage power supply to increase, the control unit is preferably designed to set each maximum value for the AC output voltage and the AC output current to a predefined highest possible maximum value, which does not change during operation, if the DC output voltage of the high-voltage power supply reaches or falls below the predefined minimum value for the DC output voltage of the high-voltage power supply. The respective maximum value for the AC output voltage and the AC output current is thus adjustable within limits, while the highest possible maximum values are predefined.

The control unit is preferably also configured to measure values of parameters such as the peak voltage of the AC output voltage and the DC offset of the AC output voltage derived from the AC output voltage and the AC output current and to compare current values of the parameters with respectively preset maximum values, and to limit an increase of the DC output voltage of the high-voltage power supply as soon as at least one preset maximum value for the DC offset and the peak voltage of the AC output voltage is reached or exceeded.

The predefined minimum value for the DC output voltage is preferably lower than 20 V and higher than 5 V.

In a preferred embodiment, the high-voltage power supply features at least one output capacitor, and the DC output voltage of the high-voltage power supply is preferably controllable by switching the high-voltage power supply on and off so that the output capacitor is either charged or not charged during operation. When the high-voltage power supply is switched on, the output capacitor is charged, and the DC output voltage of the high-voltage power supply increases. When the high-voltage power supply is not switched on, the output capacitor is discharged, and the DC output voltage of the high-voltage power supply decreases. By switching the high-voltage power supply on and off, the DC output voltage of the high-voltage power supply can thus be controlled in order to achieve the desired output values.

The high-voltage power supply preferably features a power source that supplies current to the output capacitor, and that can optionally be switched on or off.

The control unit preferably features several comparators and at least one logical gate that is connected to the outputs of the comparators, wherein the comparators are configured to compare measured current values of the AC output voltage and the AC output current and the DC output voltage with predefined maximum or minimum values, and to generate a logical output signal showing the respective comparison result, and to send this logical output signal to the at least one logical gate. The comparators, in combination with the logical gate, allow for a fast adjustment of the DC output voltage.

The invention also proposes a method of operating an electrosurgical generator comprising a high-voltage power supply, which supplies a DC output voltage, and a high-frequency part that receives the DC output voltage from the high-voltage power supply and generates a high-frequency AC output voltage and provides it at the outputs of the electrosurgical generator. The method comprises controlling the high-voltage power supply, whereby the AC output voltage of the high-frequency generator and an AC output current of the high-frequency generator are measured continuously or in a time-discrete manner.

According to the method, the DC output voltage of the high-voltage power supply continues to be increased until at least one predefined maximum value for the AC output voltage or the AC output current, or a value derived from these values, is reached or exceeded. If at least one predefined maximum value for the AC output voltage or the AC output current, or a value derived from these values, is reached or exceeded, a further increase of the DC output voltage of the high-voltage power supply is stopped, letting the DC output voltage of the high-voltage power supply decrease.

During this process, the DC output voltage of the high-voltage power supply is measured in a continuous or time-discrete manner, and the DC output voltage of the high-voltage power supply is increased as soon as the DC output voltage of the high-voltage power supply reaches or falls below a predefined minimum value for the DC output voltage of the high-voltage power supply.

Preferably, a highest possible maximum value that cannot be changed during operation is predefined for each maximum value for the AC output voltage of the high-frequency generator and the AC output current of the high-frequency generator to be preset, and each maximum value is set to the highest possible maximum value when the DC output voltage of the high-voltage power supply reaches or falls below the predefined minimum value for the DC output voltage of the high-voltage power supply.

Preferably, the values derived from the AC output voltage and the AC output current of parameters such as the peak voltage of the AC output voltage and the DC offset of the AC output voltage are measured, and current values of these parameters are compared with the respectively preset maximum values, and an increase of the DC output voltage of the high-voltage power supply is limited as soon as at least one preset maximum value for the DC offset and the peak voltage of the AC output voltage is reached or exceeded.

The minimum value for the DC output voltage is preferably set at a value between 20 V and 5V.

Control of the DC output voltage of the high-voltage power supply is preferably achieved by charging and discharging at least one output capacitor of the high-voltage power supply.

One advantage of the electrosurgical generator according to the invention and the method of operating an electrosurgical generator according to the invention is the fact that the technical limits of the generator can be better utilized to their full extent with this electrosurgical generator and this method. For example, it allows for the output of lower power or power settings of 1 W for ideally all operating modes of the electrosurgical generator.

A further advantage is the fact that the voltage does not fall below a minimum DC output voltage of the high-voltage power supply, thereby ensuring reliable operation of the high-frequency part. Otherwise, this could happen if e. g. very low power is preset.

The DC output voltage of the high-voltage power supply is monitored continuously. If the voltage falls below a permitted minimum value, a countermeasure is taken to increase the DC output voltage of the high-voltage power supply. The countermeasure preferably consists of setting the preset value for the DC output voltage of the high-voltage power supply slightly above the permitted minimum value, and all other preset values, in particular for the AC output voltage and the AC output current, but preferably also for the peak voltage of the AC output voltage and the DC offset of the AC output voltage (spark voltage) to the highest possible maximum values, so that the DC output voltage of the high-voltage power supply automatically increases again. As soon as the DC output voltage of the high-voltage power supply has increased above the permitted minimum value again, the original preset values for the AC output voltage and the AC output current, and preferably also for the peak voltage of the AC output voltage and the DC offset of the AC output voltage, are restored. With this measure, it is possible to always supply the minimum possible output power under all load conditions.

The invention includes the findings that the possible benefit of known electrosurgical generators is limited by the fact that, under certain circumstances, it cannot supply a low output power that is in principle possible and perhaps desired. The reasons for this can be, inter alia:

1) The electrosurgical generator can only be operated with permanently integrated modes. It is not easy to subsequently expand the generator by adding new instruments with new operating modes that supply lower output power because of the inherent risk that the electrosurgical generator would enter into a state in which the DC output voltage gets too low.
2) The permanent definition of a permitted minimum high-frequency AC output voltage results in an unnecessarily high-power output under certain load scenarios.

The invention will now be explained in more detail using an exemplary embodiment and referencing the figures. The figures show the following:

FIG. 1: shows a schematic diagram of some components of an electrosurgical generator for supplying an electrosurgical instrument with high-frequency AC voltage.

Figure 2:
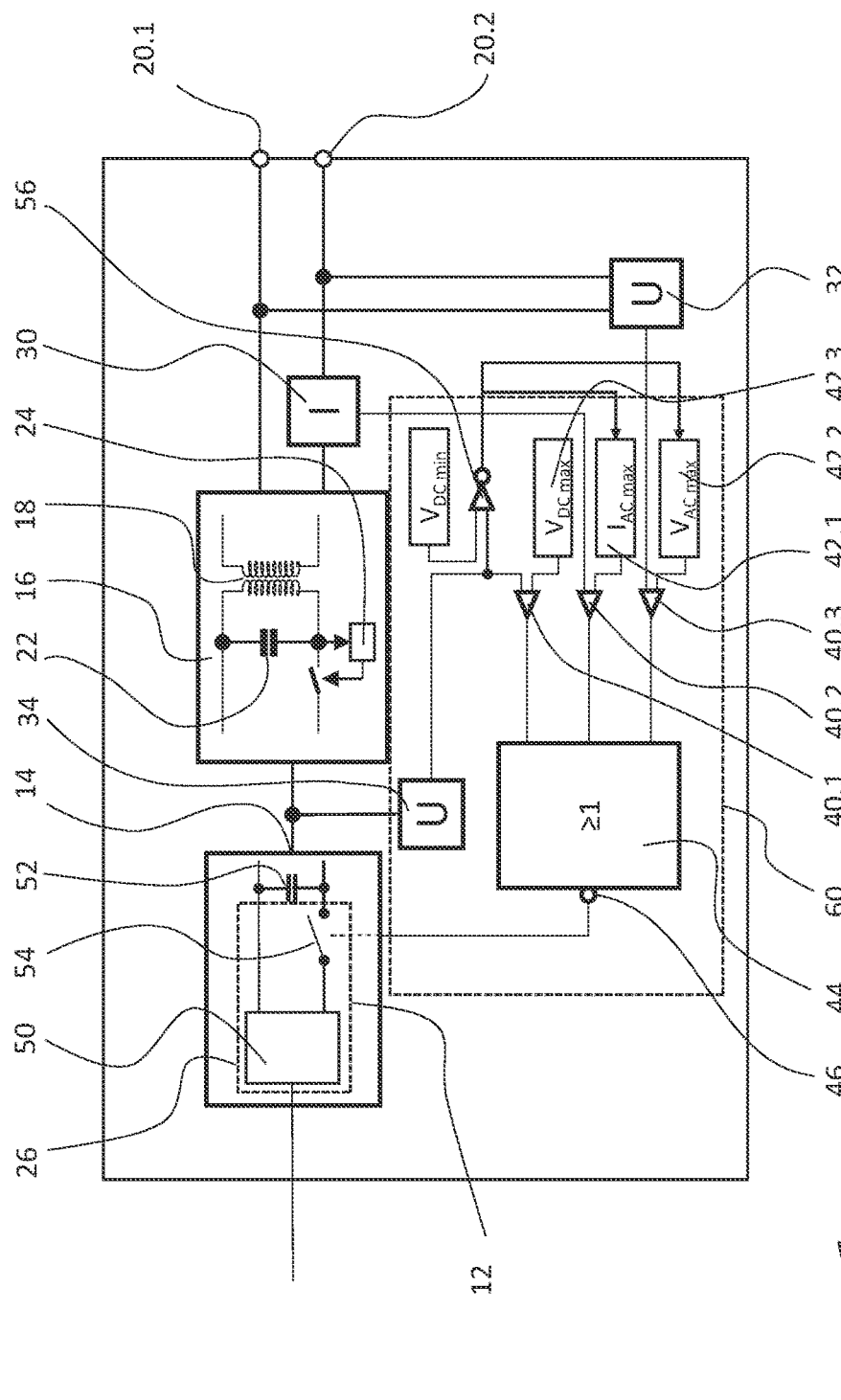

FIG. 2: shows a schematic diagram of some components of an alternative embodiment of an electrosurgical generator for supplying an electrosurgical instrument with high-frequency AC voltage.

Figure 3:
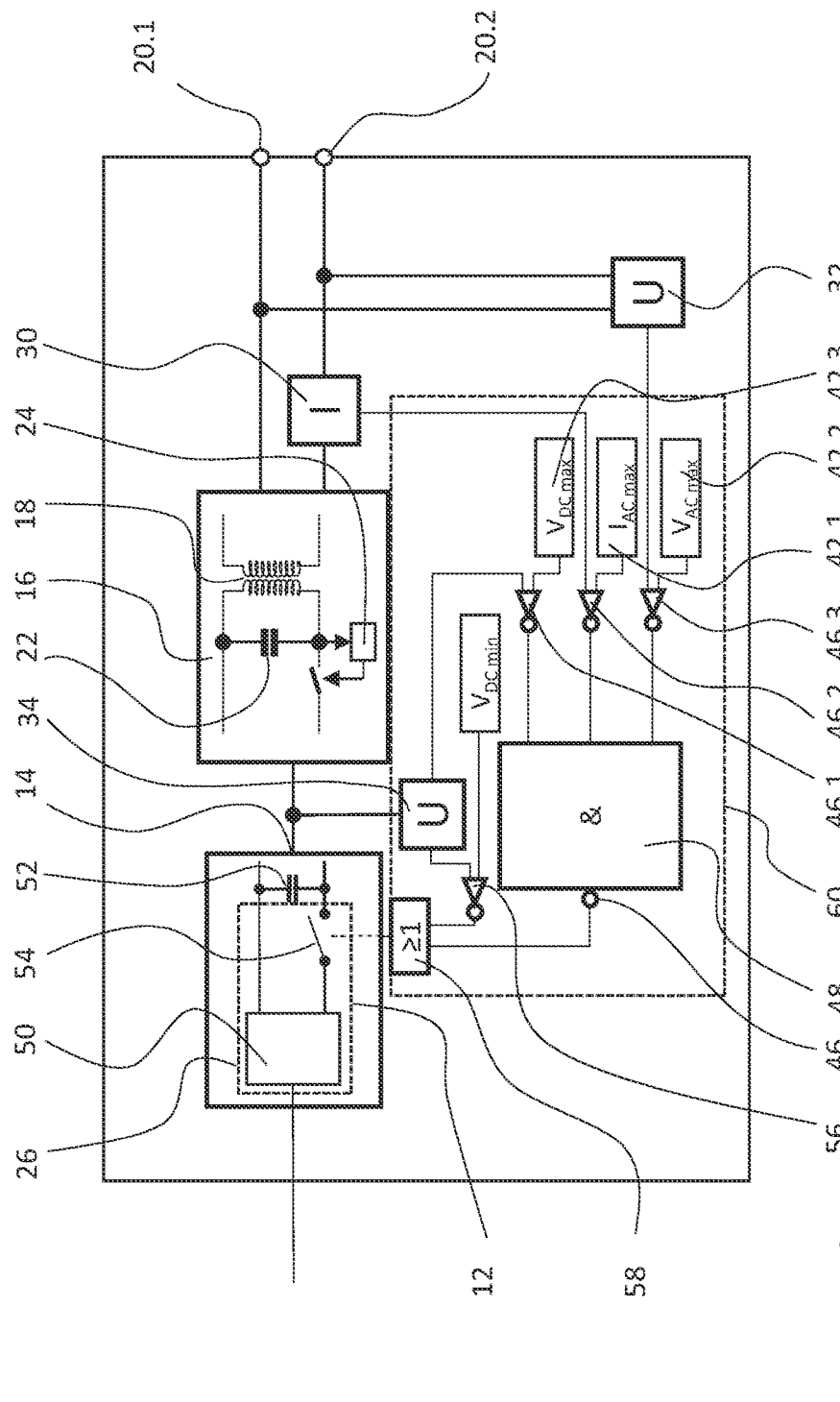

FIG. 3: shows a schematic diagram of some components of another alternative embodiment of an electrosurgical generator for supplying an electrosurgical instrument with high-frequency AC voltage.

Figure 4:
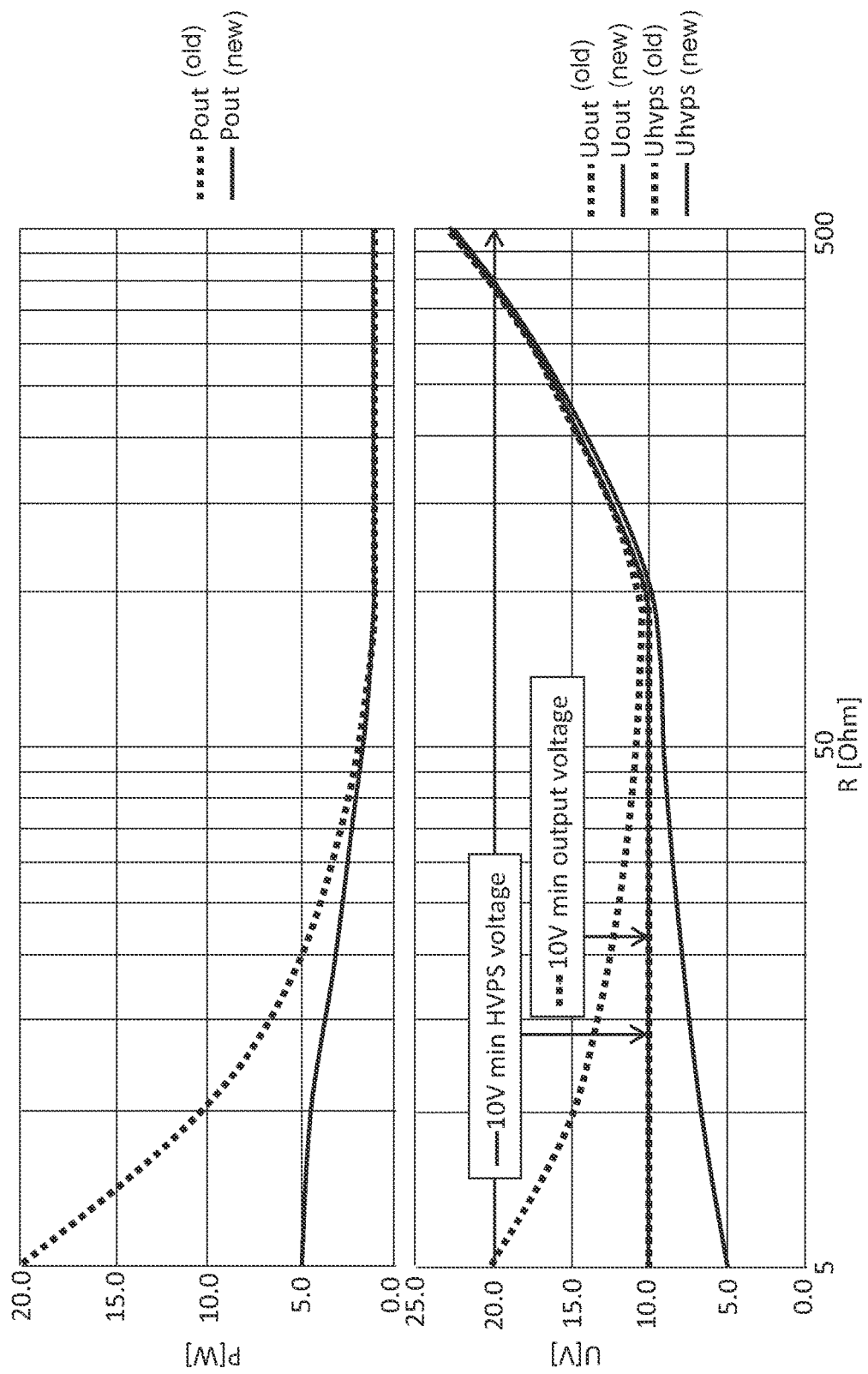

FIG. 4: shows diagrams that illustrate the power output of an electrosurgical generator according to the invention as compared to the state of the art.

FIG. 1 shows a medical device using the example of an electrosurgical generator 10. As can be seen in FIG. 1, the electrosurgical generator 10 features a high-voltage power supply 12 (HVPS) with a switchable power source 26; the HVPS can be connected to the public power grid, for example, and provides a DC output voltage at its output 14. The DC output voltage is applied to a high-frequency part 16 of the electrosurgical generator 10. The high-frequency part 16 of the electrosurgical generator 10 serves as an inverter and produces a high-frequency AC output voltage that is supplied via an output transformer 18 of the high-frequency part 16 to outputs 20.1 and 20.2 of the electrosurgical generator 10. An electrosurgical instrument can be connected to the outputs 20.1 and 20.2 of the electrosurgical generator 10.

The high-frequency part 16 of the electrosurgical generator 10 is a resonant converter in which the primary side of the output transformer 18 forms an oscillating circuit with a capacitor 22. The DC output voltage supplied by the high-voltage power supply 12 is synchronously fed into the oscillating circuit. A synchronization circuit 24 is provided for this purpose. A high-frequency AC output voltage is present at the outputs 20.1 and 20.2 during operation; the level of this AC output voltage is dependent upon the level of the DC output voltage that the high-voltage power supply 12 supplies to the high-frequency part 16. The electrosurgical generator 10 thus produces the high-frequency AC output voltage in two steps. Initially, the high-voltage power supply 12 converts the mains input voltage into a variable DC output voltage. This variable DC output voltage serves as the input voltage for the high-frequency part 16 whose AC output voltage—and thus also the AC output voltage of the electrosurgical generator 10—increases proportionally to the DC output voltage of the high-voltage power supply 12.

The AC output voltage of the electrosurgical generator 10—and with it also the AC output current and the output power—can thus be controlled by the DC output voltage generated by the high-voltage power supply 12. The DC output voltage of the high-voltage power supply 12 usually depends on a selected operating mode. Every operating mode has maximum values for the effective value of the AC output voltage via the outputs 20.1 and 20.2, of the peak output voltage via the outputs 20.1 and 20.2, of the AC output current via the outputs 20.1 and 20.2, for the DC offset in the AC output voltage via the outputs 20.1 and 20.2, as well as for the DC output voltage of the high-voltage power supply 12.

In order to measure or detect these values, an AC output current measuring unit 30, an AC output voltage measuring unit 32 and a DC output voltage measuring unit 34 are provided. The AC output voltage measuring unit 32 measures the respective momentary values of the AC output voltage at the outputs 20.1 and 20.2 and can then, based on these values, determine the effective value of the AC output voltage as well as the peak AC voltage and the DC offset in the AC output voltage. An alternative set-up would be one in which only the effective values of the AC output voltage and the AC output current as well as the peak AC voltage, but not the momentary values, are measured.

For each measured value, a maximum value is predefined for a respective operating mode. The comparators 40.1, 40.2 and 40.3 compare the respective current values measured by the measurement units 30, 32 and 34 with a respective maximum value predefined for the operating mode; see reference numbers 42.1, 42.2 and 42.3.

The initial values of the comparators 40.1, 40.2 and 40.3 are all "1" if the current value measured by a measurement unit exceeds the corresponding maximum value. Otherwise, the initial value of the respective comparators 40.1, 40.2 or 40.3 is "0". The initial values of the comparators 40.1, 40.2 and 40.3 are sent to a logically inverted OR circuit (NOR gate) 44 whose initial value at the inverted output 46 is always "0" if the output value of one of the comparators 40.1, 40.2 or 40.3 is "1"— i. e. every time one of the predefined maximum values is actually exceeded.

Inverting comparators 46.1, 46.2 and 46.3 in combination with a logical AND gate 48 can also be used instead of the comparators 40.1, 40.2 and 40.3; see FIG. 3.

The high-voltage power supply 12 is controlled by means of the output value of the inverting OR gate (NOR gate) 44. Aside from a high-voltage rectifier circuit 50 (not shown in detail here), the high-voltage power supply 12 features an output capacitor 52 that is connected to the high-voltage rectifier circuit 50 via the switch 54. Whenever the switch 54 is closed, the capacitor 52 is charged so that the voltage increases via the output capacitor 52. As soon as the switch 54 is open, the output capacitor 52 stops charging, and the voltage via the output capacitor 52 decreases again because the output capacitor 52 supplies current to the high-frequency part 16 of the electrosurgical generator 10.

Opening and closing of the switch 54 is directly or indirectly controlled by the output signal of the inverting OR gate (NOR gate) 44 or the AND gate 48. Whenever the output value of the NOR gate 50 or of the AND gate 48 is "0", the switch 54 is open and the output capacitor 52 stops charging. Whenever the output value of the NOR gate 44 or of the AND gate 48 is "1", the switch 54 is closed and the output capacitor 52 keeps charging so that the output voltage of the high-voltage power supply 12 increases again.

It should be noted that the switch does not necessarily have to be implemented or implemented as indicated. The switch rather represents a switchable current source that is switched on or off via the control signal (that controls the switch 54 in the illustration).

Controlled opening and closing of the switch 54 or controlled switching on and off of the current source makes it possible to always control the DC output voltage of the high-voltage power supply 12 when the electrosurgical generator 10 is in operation so that one of the predefined maximum values is reached—at least for as long as the load at the outputs 20.1 and 20.2 permits. As soon as one of the predefined maximum values is exceeded—and not all values are therefore below the predefined maximum values— charging of the output capacitor 52 is interrupted so that the voltage via this capacitor decreases again—until all values are again below the predefined maximum values and the switch 54 is closed again.

The invention stipulates to also predefine a lower threshold value for the DC output voltage of the high-voltage power supply 12 and to generate a control signal for the switch 54; this control signal causes the switch 54 to always close as soon as the predefined minimum value for the DC output voltage of the high-voltage power supply 12 is reached or if the voltage falls below the predefined minimum value. An inverting comparator 56 is provided for this purpose whose output value is always "1" if the DC output voltage at output 14 of the high-voltage power supply 12 falls below the predefined minimum value.

According to the embodiments shown in FIGS. 1 and 3, the output value of this inverting comparator 56, just like the output value of the NOR gate 44, is sent to a further OR gate 58 whose output value is always "1" if either the output value of the NOR gate 44 or the output value of the inverting comparator 56 is "1".

FIG. 2 shows an alternative embodiment in which the output value of the inverting comparator 56 is not directly used for switching the switch 54, but rather causes an increase of the maximum values for the AC output voltage and the AC output current, and possibly values derived therefrom, to predefined highest possible maximum values of these parameters as soon as the preset minimum value for the DC output voltage of the high-voltage power supply 12 is reached or the voltage falls below this value.

A suitable minimum value for the DC output voltage of the high-voltage power supply 12 is typically between 5V and 10 V.

The comparators and logical gates thus form a hardware control node; they can be implemented in hardware or software. The hardware control node is part of a control unit 60. The comparators and logical gates operate continuously, for example, but they can also be implemented as time-discrete gates.

The hardware control node composed of OR-linked comparators generates a binary control signal for the high-voltage power supply 12 that indicates whether the output capacitor 52 of the high-voltage power supply 12 is to be charged or not. If the output signal of the hardware control node is "1", the output capacitor 52 is charged, otherwise it is not charged. The output signal of the hardware control node is not clocked and is basically scanned by the clocked high-voltage power supply 12 with its clock pulse.

To increase the range of operating modes of the electrosurgical generator 10, it is desirable that preferably all operating modes of the electrosurgical generator 10 can be operated with power settings of 1 watt.

In principle, controlling the output power by setting the input voltage at the high-frequency part 16 is done by setting the DC output voltage (HVPS voltage) of the high-voltage power supply 12. As described above, the high-frequency part 16 of the electrosurgical generator 10 is a resonant converter that generates the high-frequency AC output voltage, which can be supplied at the outputs 20.1 and 20.2 of the electrosurgical generator to an electrosurgical instrument connected thereto, from the DC output voltage of the high-voltage power supply 12. The DC output voltage of the high-voltage power supply 12 is set via a software interface using the hardware control node comprising the comparators and the logical gates. The following maximum values for the following parameters can be predefined via the software interface:

effective value of the AC output voltage
peak value of the AC output voltage
effective value of the AC output current
DC voltage component in the AC output voltage (spark voltage; DC offset)
DC output voltage of the high-voltage power supply (HVPS voltage)

The software predefines the maximum values based on the measured values and the selected operating mode.

The hardware control node controls, according to the predefined threshold values, the generation of the DC output voltage of the high-voltage power supply 12 (see above), from which the high-frequency part 16 in turn generates the AC output voltage of the electrosurgical generator 10 in accordance with the preset power level. Low output power correspondingly requires low DC output voltages of the high-voltage power supply 12. However, the DC output voltage of the high-voltage power supply 12 should not fall below a critical value.

To ensure that this requirement is fulfilled, the state of the art stipulates the following:

The electrosurgical generator is only operated with firmly integrated modes.
Low power settings are not permitted for specific critical operating modes.
The high-frequency power controller cannot fall below a globally defined and load-independent high-frequency output voltage. The state of the art defines the high-frequency power controller as a PID controller, implemented in the form of software, that compares the measured power output with a nominal output and uses the output voltage as a manipulated variable.

By providing a control of the high-voltage power supply, and taking into consideration the value of the DC output voltage of the high-voltage power supply 12 and a predefined minimum value for the DC output voltage of the high-voltage power supply 12, it is possible to override the above-mentioned limitations at least partially if a sufficiently high DC output voltage of the high-voltage power supply 12 is ensured by other means—namely, in particular, by the comparator 56 and the OR gate 58.

FIG. 4 shows that, with a power setting of 1 W (which is only possible for very few modes of an electrosurgical generator according to the state of the art), the output power of an electrosurgical generator according to the state of the art will undesirably increase to up to 20 W even with loads of less than 50 ohms. With the electrosurgical generator 10 according to the invention, considerably lower output power values are possible with small load resistance values (e. g. 5 W instead of 20 W at 5 ohms). For an electrosurgical generator according to the state of the art, the AC output voltage must not fall below 10 V, which means that a load of 5Ω will result in 20 W of power that is associated with a DC output voltage of 20 V; see dotted lines in the diagrams. With an electrosurgical generator according to the invention, only the DC output voltage must not fall below 10 V, but the AC output voltage can fall below 10 V. This results in an AC output voltage of 5 V at a load of 5Ω, and a supplied power of 5 W; see solid lines in the diagrams.

The lower diagram shows two lines, of which the line displayed for lower voltage values represents the AC output voltage, and the line displayed for higher voltage values represents the DC output voltage.

It follows from the above description that a method of operating an electrosurgical generator comprises the following steps:

The DC output voltage of the high-voltage power supply is increased until at least a predefined maximum value for the DC output voltage or the AC output current, or a value derived from these values, is reached or exceeded.
If at least one predefined maximum value for the AC output voltage or the AC output current, or a value derived from these values, is reached or exceeded, a further increase of the DC output voltage of the high-voltage power supply is stopped, letting the DC output voltage of the high-voltage power supply decrease.
The DC output voltage of the high-voltage power supply is measured continuously or in a time-discrete manner, and the DC output voltage of the high-voltage power supply is increased as soon as the DC output voltage of the high-voltage power supply reaches or falls below a predefined minimum value for the DC output voltage of the high-voltage power supply.

For each maximum value to be predefined for the AC output voltage of the high-frequency generator and for the AC output current of the high-frequency generator, a highest possible maximum value that cannot be changed during operation is preferably predefined, and each maximum value is set to the respective highest possible maximum value if the DC output voltage of the high-voltage power supply reaches or falls below the predefined minimum value for the DC output voltage of the high-voltage power supply. This causes the DC output voltage of the high-voltage power supply 12 to increase again.

Preferably, values of parameters like the peak voltage of the AC output voltage and the DC offset of the AC output voltage are derived from the AC output voltage and the AC output current, and current values of these parameters are compared with the respectively preset maximum values. However, the peak voltage of the AC output voltage and the DC offset of the AC output voltage can also be measured directly instead of being derived from the AC output voltage and the AC output current. An increase of the DC output voltage of the high-voltage power supply is limited as soon as at least one preset maximum value for the DC offset and the peak voltage of the AC output voltage is reached or exceeded.

LIST OF REFERENCE NUMBERS 10 electrosurgical generator
12 high-voltage power supply
16 high-frequency part
18 output transformer 20.1, 20.2 outputs
22 capacitor
24 synchronization circuit
26 switchable current source
30 AC output current measuring unit
32 AC output voltage measuring unit
34 DC output voltage measuring unit
40.1, 40.2, 40.3 comparators
42.1, 42.2, 42.3 predefined maximum values for the parameters
44 OR circuit (NOR gate)
46 inverted output
46.1, 46.2, 46.3 alternative comparators
48 AND gate
50 high-voltage rectifier circuit
52 output capacitor
54 switch
56 inverting comparator
58 OR gate (NOR gate)
60 control unit

The invention claimed is:

1. An electrosurgical generator comprising:
a high-voltage power supply configured to supply a DC output voltage during operation; and
a high-frequency part configured to receive the DC output voltage of the high-voltage power supply during operation, and generate a high-frequency AC output voltage and provide it to the outputs of the electrosurgical generator;
an AC output voltage measuring unit;
an AC output current measuring unit;
a DC output voltage measuring unit; and
a control unit connected to the AC output voltage measuring unit, AC output current measuring unit, and DC output voltage measuring unit, and configured to:
(i) respectively receive, when the electrosurgical generator is in operation, signals from the AC output voltage measuring unit and the AC output current measuring unit, which represent a respective current value of the AC output voltage and the AC output current,
compare the respective current values of the AC output voltage and the AC output current with predefined maximum values for the AC output voltage and the AC output current, and
limit an increase of the DC output voltage of the high-voltage power supply as soon as at least one predefined maximum value for the AC output voltage or the AC output current, or a value derived from these values, is reached or exceeded; and
(ii) receive when the electrosurgical generator is in operation, signals from the DC output voltage measuring unit, which represent a respective current value of the DC output voltage,
compare a respective current value of the DC output voltage with a predefined minimum value for the DC output voltage, and
cause the DC output voltage of the high-voltage power supply to increase as soon as the voltage falls below the predefined minimum value for the DC output voltage.

2. The electrosurgical generator according to claim 1, wherein the control unit is further configured to set each maximum value for the AC output voltage and the AC output current to a predefined highest possible maximum value that cannot be changed during operation, if the DC output voltage of the high-voltage power supply reaches or falls below the predefined minimum value for the DC output voltage of the high-voltage power supply.

3. The electrosurgical generator according to claim 1, wherein the control unit is further configured to:
detect current values of parameters derived from the AC output voltage and the AC output current and compare the current values of the parameters with respectively preset maximum values, and
limit an increase of the DC output voltage of the high-voltage power supply as soon as at least one preset maximum value for the parameters is reached or exceeded.

4. The electrosurgical generator according to claim 1, wherein the predefined minimum value for the DC output voltage is lower than 20 V and higher than 5V.

5. The electrosurgical generator according to claim 1, wherein the high-voltage power supply comprises an output capacitor that is configured to be charged or not charged during operation, thereby controlling the DC output voltage of the high-voltage power supply by switching the high-voltage power supply on and off.

6. The electrosurgical generator according to claim 5, wherein the high-voltage power supply comprises a current source that feeds into the output capacitor and is configured to be switched on or off.

7. The electrosurgical generator according to claim 1, wherein the control unit comprises:
a logical gate; and
a plurality of comparators configured to:
compare the measured current values of the AC output voltage and the AC output current and the DC output voltage with predefined maximum or minimum values, and
generate a logical output signal showing a respective comparison result, and send this signal to the logical gate.

8. A method of operating an electrosurgical generator with a high-voltage power supply that supplies a DC output voltage, and a high-frequency part that receives the DC output voltage of the high-voltage power supply and generates a high-frequency AC output voltage, which it then provides at the outputs of the electrosurgical generator, the method comprising:
measuring the AC output voltage of the high-frequency generator, an AC output current of the high-frequency generator, and the DC output voltage of the high-voltage power supply continuously or in a time-discrete manner;
comparing a respective current value of the DC output voltage with a predefined minimum value for the DC output voltage; and
controlling the high-voltage power supply to:
continuously increase the DC output voltage of the high-voltage power supply until at least a predefined maximum value for the DC output voltage or the AC output current, or a value derived from these values, is reached or exceeded;
if at least one predefined maximum value for the AC output voltage or the AC output current, or a value derived from these values, is reached or exceeded, stop a further increase of the DC output voltage of the high-voltage power supply and let the DC output voltage of the high-voltage power supply decrease; and
increase the DC output voltage of the high-voltage power supply as soon as the DC output voltage of the high-voltage power supply reaches or falls below the predefined minimum value for the DC output voltage of the high-voltage power supply.

9. The method according to claim 8, further comprising:
if the DC output voltage of the high-voltage power supply reaches or falls below the predefined minimum value for the DC output voltage of the high-voltage power supply, setting each maximum value to be predefined for the AC output voltage of the high-frequency generator and the AC output current of the high-frequency generator to a highest possible maximum value that cannot be changed during operation is predefined.

10. The method according to claim 8, further comprising:
comparing current values of parameters derived from the AC output voltage and the AC output current with the respectively preset maximum values; and
controlling the high-voltage power supply to limit an increase of the DC output voltage of the high-voltage power supply as soon as at least one preset maximum value for a DC offset and the peak voltage of the AC output voltage is reached or exceeded.

11. The method according to claim 8, wherein the predefined minimum value for the DC output voltage is a value between 20 V and 5V.

12. The method according to claim 8, wherein the DC output voltage of the high-voltage power supply is increased by letting at least one output capacitor of the high-voltage power supply charge.

13. The electrosurgical generator according to claim 3, wherein the parameters include a peak voltage of the AC output voltage and a DC offset of the AC output voltage.

* * * * *